(12) United States Patent
Shalaby

(10) Patent No.: US 6,699,940 B2
(45) Date of Patent: Mar. 2, 2004

(54) CYANOACRYLATE-CAPPED HETEROCHAIN POLYMERS AND TISSUE ADHESIVES AND SEALANTS THEREFROM

(75) Inventor: Shalaby W. Shalaby, Anderson, SC (US)

(73) Assignee: Poly Med, Inc., Anderson, SC (US)

( * ) Notice: Subject to any disclaimer, the term of this patent is extended or adjusted under 35 U.S.C. 154(b) by 0 days.

(21) Appl. No.: 10/300,079

(22) Filed: Nov. 20, 2002

(65) Prior Publication Data

US 2003/0105256 A1 Jun. 5, 2003

Related U.S. Application Data

(60) Provisional application No. 60/335,439, filed on Dec. 4, 2001.

(51) Int. Cl.$^7$ ............................................. C08F 265/04
(52) U.S. Cl. ..................... 525/308; 526/297; 526/298; 526/310; 526/312; 526/319; 525/255; 525/295; 525/302
(58) Field of Search ............................... 526/297, 298, 526/310, 312, 319; 525/255, 295, 302, 308

(56) References Cited

U.S. PATENT DOCUMENTS

| | | | | | |
|---|---|---|---|---|---|
| 4,260,719 | A | * | 4/1981 | Ching | 528/196 |
| 4,377,490 | A | * | 3/1983 | Shiraishi et al. | 252/188.3 R |
| 5,340,873 | A | * | 8/1994 | Mitry | 525/10 |
| 5,350,798 | A | | 9/1994 | Linden et al. | 525/41 |
| 5,373,035 | A | * | 12/1994 | Uemura et al. | 523/212 |
| 5,422,068 | A | | 6/1995 | Shalaby et al. | 422/22 |
| 5,653,992 | A | | 8/1997 | Bezwada et al. | 264/4.3 |
| 5,714,159 | A | | 2/1998 | Shalaby | 424/426 |
| 6,299,631 | B1 | | 10/2001 | Shalaby | 606/214 |
| 6,462,169 | B1 | | 10/2002 | Shalaby | 528/354 |
| 6,467,169 | B1 | | 10/2002 | Wieres | 29/890 |

* cited by examiner

*Primary Examiner*—Helen L. Pezzuto
(74) *Attorney, Agent, or Firm*—Leigh P. Gregory

(57) ABSTRACT

The present invention is directed toward cyanoacrylate-based tissue adhesive or sealant compositions comprising cyanoacrylate-capped heterochain polymers, such as those comprising one or more oxyalkylene, alkylene carbonate, and ester-units derived from cyclic lactones. Such compositions can be radiochemically sterilized and used in repairing internal organs or tissue blocking body conduits.

17 Claims, No Drawings

CYANOACRYLATE-CAPPED HETEROCHAIN POLYMERS AND TISSUE ADHESIVES AND SEALANTS THEREFROM

The present application claims priority to earlier filed Provisional Application, U.S. Ser. No. 60/335,439 filed on Dec. 4, 2001.

BACKGROUND TO THE INVENTION

The exceptionally fast rate of anionic polymerization of cyanoacrylates in the presence of a base, including water, made this class of monomers unique among all acrylic and vinyl monomers. Of the alkyl cyanoacrylate family of monomers, the methyl- and ethyl-esters are used extensively in industrial and consumer-type adhesives. Meanwhile, the isobutyl, n-butyl, and n-octyl cyanoacrylate esters are used clinically as blocking agents, sealants, and/or tissue adhesives in different parts of the world due to their much lower toxicity as compared with their more reactive methyl and ethyl counterparts. In the past few decades, there has been a great deal of interest in using tissue adhesives in many surgical procedures in favor of sutures and staples for a variety of reasons, including (1) ease of application and reduced clinician time; (2) location of repairable site as in contoured locations; (3) biomechanical properties as in weak organs, such as liver and pancreas; and (4) minimized hypertrophy and scar formation as in plastic surgery. However, there have been also a number of concerns associated with the alkyl cyanoacrylates. These include (1) their low viscosity and associated difficulties in precise delivery at the application site in non-medical and medical applications; (2) poor shear strength of the adhesive joint, particularly in aqueous environments in both medical and non-medical applications; (3) high modulus or stiffness of cured polymers at soft tissue application sites and associated mechanical incompatibility, which can lead to adhesive joint failure and/or irritation of the surrounding tissue; (4) excessive heat generation upon application of monomers to living tissue due to exceptionally fast rate of curing resulting in necrosis; and (5) site infection, among other pathological complications, associated with prolonged residence of the non-absorbable tissue adhesives. In response to these concerns, and particularly the ones associated with the non-absorbable cyanoacrylate that are used clinically, Shalaby and Linden (U.S. Pat. No. 5,350,798) disclosed a novel, absorbable tissue adhesive compositions that addressed, to a practical extent, the drawbacks of the absorbable as well as non-absorbable cyanoacrylates. In effect, the absorbable tissue adhesive compositions disclosed in U.S. Pat. No. 5,350,798, were based (1) primarily on a methoxy alkylcyanoacrylate and preferably methoxypropyl cyanoacrylate as the precursor of an absorbable tissue adhesive polymer; and (2) a polymeric, highly absorbable, liquid comprising an oxalate ester of triethylene glycol as a modifier to modulate the viscosity of the overall composition, lower the heat of polymerization, and increase the compliance and absorption rate of the cured adhesive joint. In a recent disclosure by this inventor (U.S. Pat. No. 6,299,631), a number of other useful modifiers were described and the functional performance of the new adhesive compositions was reported.

Although the admixture of polymeric modifier has been shown to be effective in addressing most of the medical and non-medical drawbacks of cyanoacrylate-based adhesives represented by methoxy propyl cyanoacrylate, there remain a number of technical drawbacks that exist in these systems. Such drawbacks disadvantage cyanoacrylates as precursors of absorbable and non-absorbable adhesives in both medical and non-medical applications and are due to having a mixture of two or more polymers or precursors thereof. This is related to the fact that the polymeric modifier(s) is usually present as a solute in the cyanoacrylate before application, but phase separation of the modifier may take place as the polycyanoacrylate is formed due to mutual immiscibility of two or more polymers, a common phenomenon associated with polymer miscibility. Naturally, there are a few exceptions to this phenomenon, and carefully chosen polymeric modifiers with specially tailored chains and monomeric cyanoacrylate may remain as a one-phase system after the latter is polymerized. This may very well be the case in some examples cited in U.S. Pat. Nos. 5,350,798 and 6,299,631. Nevertheless, the likelihood of encountering immiscibility in the formed adhesive joint can compromise not only the adhesive, but also the cohesive properties of such joint. This created a distinct need for the novel design of tissue adhesive/sealant compositions, subject of this invention, comprising covalently linked components in the cured adhesive joint or sealant. In effect, this invention deals with precursors of tissue adhesives/sealants (PT-A/S) as prepared as single-phase liquids that cure into their final functional forms as a homogeneous material, and not a physical mixture of two or more separable components. Moreover, the precursors of these compositions are designed to contain in one molecule two or more cyanoacrylate functionalities capable of fast anionic polymerization in aqueous environments (or in presence of a weak base), that are covalently linked to heterochain polymeric components responsible for most or all of the modulating features described in U.S. Pat. Nos. 5,350,798 and 6,299,631 without contending with the drawbacks of the aforementioned physical mixtures. Such design is applicable to both absorbable and non-absorbable cyanoacrylate-based adhesives/sealants for non-medical or medical applications.

SUMMARY OF THE INVENTION

This invention deals with a cyanoacrylate-based tissue adhesive or sealant composition comprising a cyanoacrylate-capped heterochain polymer having two or more cyanoacrylate ester groups per chain. The heterochain polymer used for capping can be one or more absorbable polymer of the following types: polyester, polyester-carbonate, polyether-carbonate, and polyether-ester. The capped polymer can also be derived from a polyalkylene glycol such as polyethylene glycol, or a block copolymer of polyethylene glycol and polypropylene glycol. Capping of the heterochain polymer can be achieved using an alkyl cyanoacrylate, or an alkoxyalkyl cyanoacrylate such as ethyl cyanoacrylate or methoxypropyl cyanoacrylate, respectively, in the presence of phosphorus-based acids or precursors thereof, such as pyrophosphoric acid and polyphosphoric acid in amounts exceeding 10 ppm. The formulations, subject of this invention, are intended for use as tissue adhesives or sealants for topical application. Radiochemically sterilized formulations, subject of this invention, can also be used as sterile adhesives, sealants, or blocking agents in repairing mechanically or pathologically compromised internal organs or tissues, or in blocking body conduits, such as blood vessels.

DETAILED DESCRIPTION OF PREFERRED EMBODIMENTS

This invention deals with cyanoacrylate-capped heterochain polymers with two or more cyanoacrylate functionalities per molecule and their use as absorbable or non-absorbable tissue adhesives, sealants, blocking agents, and/or hemostatic adhesives in medical or non-medical applications. Another aspect of this invention deals with a cyanoacrylate-based composition comprising a cyanoacrylate-capped heterochain polymer and a stabilizer against premature anionic polymerization such as pyrophosphoric acid and polyphosphoric acid and preferably an organic dye. One aspect of this invention deals with covalent binding of a cyanoacrylate functionality to a heterochain polymer molecule. A more specific feature of this aspect is using the process of transesterification between a hydroxyl group and a simple cyanoacrylate ester, such as methyl cyanoacrylate (MC), ethyl cyanoacrylate (EC), and methoxypropyl cyanoacrylate (MPC) to yield a cyanoacrylate-capped heterochain polymer in the presence of catalytic amounts of pyrophosphoric acid or polyphosphoric acid at a concentration that exceeds 10 ppm. Another aspect of this invention deals with the preparation of cyanoacrylate-capped (CC) polyalkylene oxide or copolymers thereof to produce a range of anionically fast polymerizing CC polyethers with a broad range of hydrophilic/hydrophobic content. In one more aspect of this invention, the linear polyether-esters described by this inventor in U.S. Pat. Nos. 5,653,992 and 5,714,159, as absorbable liquid gel-formers are capped with cyanoacrylate to produce unique adhesive sealants that undergo liquid to gel physical transformation as well as a covalently linked network. Another aspect of this invention deals with the preparation of absorbable liquid PT-A/S comprising CC linear or branched polyester carbonate, such as those made from trimethylene carbonate and other cyclic monomers, such as lactide, glycolide, p-dioxanone, 1,5-dioxepan-2-one. A more specific aspect of this invention is that the capped polyester-carbonate is made using a polyfunctional hydroxylic initiator. A typical example of this product is a polyaxial copolyester-carbonate (PAX) made by first forming a polymeric initiator through the ring-opening polymerization of a mixture of caprolactone and trimethylene carbonate in the presence of trimethylolpropane and a catalytic amount of stannous octoate. This is followed by end-grafting the resulting product with l-lactide. Another aspect of this invention deals with CC linear polyalkylene oxalate as an absorbable PT-A/S. Another aspect of this invention deals with CC polytrimethylene glutarate as non-absorbable PT-A/S. Another aspect of this invention deals with mixtures of one or more of the PT-A/S described herein. Another aspect of this invention deals with mixtures of one or two PT-S/A described herein with one or more cyanoacrylate, wherein the cyanoacrylate is an alkyl or alkoxyalkyl ester. Another aspect of this invention deals with the process of preparing the PT-A/S described herein. Another aspect of this invention deals with the use of the PT-A/S described herein as tissue adhesives for skin closure, absorbable or non-absorbable tissue adhesive for adjoining naturally derived patches (e.g., elastin) to mechanically compromised walls of an internal organ. This may entail sealing an accidental hole or surgically created hole in living organs, such as the duodenum, esophagus, trachea, lung, large intestine, tympanic membrane, and blood vessels. Another aspect of this invention deals with the use of PT-A/S as a sealing barrier (with and without a bioactive agent) for vascular grafts, such as those made of polyethylene terephthalate or microporous Teflon. Another aspect of this invention deals with the use of PT-A/S as medicated or non-medicated barriers for preventing or minimizing the incidence of post-operative adhesion. Another aspect of this invention is the use of PT-A/S as a suture or staple adjuvants to minimize the number of the mechanical ligatures per cm of the repaired wound. Another aspect of this invention is the use of PT-A/S as (1) a sealant of a punctured vascular wall; (2) endovascular stent, both absorbable and non-absorbable; (3) as an absorbable plug or blocking agent of a biological conduit; and (4) stent in repaired ureter.

Another aspect of this invention deals with preparing sterile adhesive or sealant formulations using radiochemical sterilization as per U.S. Pat. No. 5,422,068.

The above list of CC compositions and their uses is by no means exhaustive and can be easily extended by those familiar with the art of tissue adhesives and sealants.

Further illustrations of the present invention are provided in the two examples cited below.

EXAMPLE 1
Preparation and Curing of a Tissue Adhesive Formulation Comprising Cyanoacrylate-Capped Polyethylene Glycol-600 (PEG-600)

Predried PEG-600 (20 g) is mixed with ethyl cyanoacrylate (20 g) containing 20 mg of pyrophosphoric acid under a dry nitrogen atmosphere in a glass reactor equipped for stirring. The reaction is allowed to proceed by heating for 5 hours at 85° C. and then cooled to room temperature. The resulting formulation is characterized for identity by IR and adhesive properties [using the fabric peel test described by J. D. Kline in the Sixth World Congress, Trans. Soc. Biomat., III, 1062 (2000)]. Its gelation in the presence of a buffered solution at pH 7.4 is confirmed.

EXAMPLE 2
Preparation and Curing of Tissue Adhesive Comprising Cyanoacrylate-capped Triaxial Poly ($\epsilon$-caprolactone-co-trimethylene Carbonate) (TCT) and Ethyl Cyanoacetate (EC)

This was pursued in two steps

Step One—50 g of low molecular weight 50/50 poly($\epsilon$-caprolactone-co-trimethylene carbonate) is prepared using a stoichiometric amount of trimethylol propane as the initiator [to produce a copolymer having a number average molecular weight ($M_n$) of about 3000 Da (as determined by GPC) and stannous octoate (5 mg) as a catalyst. The polymerization is completed by heating the reactants under dry nitrogen while stirring at 160° C. for 4–5 hours until practically complete conversion is achieved. Traces of unreacted monomer are removed by heating the reaction product under reduced pressure at 80° C. The cooled product is then analyzed by GPC to confirm its $M_n$ to be 3200 Da.

Step Two—The CC-capping of TCT (10 g) from Step 1 is conducted in the presence of 20 g ethyl cyanoacrylate and 20 mg of pyrophosphoric acid as per the procedure of Example 1. The final product is characterized as in Example 1.

Formation of a water insoluble product of the formulation is achieved by pouring the liquid product onto a buffer solution of pH 7.4.

EXAMPLE 3
Preparation of Tissue Adhesive Formulations Comprising CC-capped Polyaxial Polyester (PAX) and Methoxypropyl Cyanoacrylate (MPC)

This was pursued in two steps

Step One: Polymerization of PAX—A polyaxial polymeric initiator was first prepared by copolymerization of 5/20/25 (molar) of glycolide (G), $\epsilon$-caprolactone (CL), and trimethylene carbonate (TMC) in the presence of stannous octoate and trimethylol propane as a catalyst and monomeric initiator, respectively, as described in U.S. Pat. No. 6,462,169. The polyaxial polymeric initiator was then grafted with l-lactide (LL) to yield a segmented, partially crystalline polymer comprising sequences derived from G, CL, TMC, and LL at a ratio of 5/20/25/50. The segmented copolymer was isolated and purified as per U.S. Pat. No. 6,467,169, and then characterized for identity (IR and NMR) molecular weight (GPC) and thermal properties (DSC).

Step Two: CC-capping of PAX in the Presence of Methoxypropyl Cyanoacrylate (MPC)—In a predried reactor equipped for mechanical stirring, PAX (10.5 g) was mixed under dry nitrogen atmosphere with MPC (21 g) containing 20 mg of pyrophosphoric acid at 110° C. for 5 hours. At the conclusion of this period, the resulting formulation was cooled to 25° C. and characterized as described in Example 1.

EXAMPLE 4
Preparation of Tissue Adhesive Formulation Comprising CC-capped Polyaxial Polyester (PAX) and EC This was conducted under similar conditions to those used in Example 3, with the exception of using EC instead of MPC and 85° C. as the reaction temperature in the second step.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A curable, liquid, cyanoacrylate-based composition comprising a cyanoacrylate-capped heterochain polymer having at least two cyanoacrylate ester groups per chain.

2. A curable, liquid, cyanoacrylate-based composition as in claim 1 wherein the heterochain polymer is selected from the group consisting of absorbable polyester, polyester-carbonate, polyether-carbonate, and polyether-ester.

3. A curable, liquid, cyanoacrylate-based composition as in claim 1 wherein the heterochain polymer is a polyether selected from the group consisting of polyethylene glycol, polypropylene glycol, and a block copolymer of polyethylene glycol and polypropylene glycol.

4. A curable, liquid, cyanoacrylate-based composition as in claim 1 admixed with a monomer selected from the group consisting of alkyl-cyanoacrylate and alkoxyalkyl-cyanoacrylate.

5. A curable, liquid, cyanoacrylate-based composition as in claim 1 wherein the cyanoacrylate-capping is achieved with greater than 10 ppm of pyrophosphoric or polyphosphoric acid.

6. A curable, liquid, cyanoacrylate-based composition as in claim 2 wherein the cyanoacrylate-capping is achieved with greater than 10 ppm of pyrophosphoric or polyphosphoric acid.

7. A curable, liquid, cyanoacrylate-based composition as in claim 3 wherein the cyanoacrylate-capping is achieved with greater than 10 ppm of pyrophosphoric or polyphosphoric acid.

8. A curable, liquid, cyanoacrylate-based composition as in claim 4 wherein the cyanoacrylate-capping is achieved with greater than 10 ppm of pyrophosphoric or polyphosphoric acid.

9. A curable, liquid, cyanoacrylate-based composition as in claim 1 colored with an organic dye.

10. A curable, liquid, cyanoacrylate-based composition as in claim 6 colored with an organic dye.

11. A curable, liquid, cyanoacrylate-based composition as in claim 1 wherein the cyanoacrylate-capped heterochain polymer having at least two hydroxy end groups per chain is made by a method comprising the step of reacting a heterochain polymer with a member selected from the group consisting of an alkyl cyanoacrylate and a substituted alkyl cyanoacrylate in the presence of pyrophosphoric or polyphosphoric acid.

12. A curable, liquid, cyanoacrylate-based composition as in claim 11 wherein the heterochain polymer is reacted with an alkyl cyanoacrylate.

13. A curable, liquid, cyanoacrylate-based composition as in claim 12 wherein the alkyl cyanoacrylate comprises ethyl cyanoacrylate.

14. A curable, liquid, cyanoacrylate-based composition as in claim 11 wherein the heterochain polymer is reacted with an alkyl substituted cyanoacrylate.

15. A curable, liquid, cyanoacrylate-based composition as in claim 14 wherein the alkyl substituted cyanoacrylate comprises methoxypropyl cyanoacrylate.

16. A curable, liquid, cyanoacrylate-based composition as in claim 1 employed for topical application as a tissue adhesive or sealant.

17. A curable, liquid, cyanoacrylate-based composition as in claim 1 that is radiochemically sterilized for use as a sterile adhesive or sealant in repairing compromised internal organs or tissues.

* * * * *